US009510994B2

(12) United States Patent
Wilford et al.

(10) Patent No.: US 9,510,994 B2
(45) Date of Patent: Dec. 6, 2016

(54) THERAPEUTIC WRAP WITH PATTERN ZONE

(71) Applicants: Michael L Wilford, Chicago, IL (US); Fernando A. Ubidia, Ludlow, MA (US)

(72) Inventors: Michael L Wilford, Chicago, IL (US); Fernando A. Ubidia, Ludlow, MA (US)

( * ) Notice: Subject to any disclaimer, the term of this patent is extended or adjusted under 35 U.S.C. 154(b) by 433 days.

(21) Appl. No.: 14/175,790

(22) Filed: Feb. 7, 2014

(65) Prior Publication Data

US 2015/0224015 A1    Aug. 13, 2015

(51) Int. Cl.
*A61H 9/00*      (2006.01)
*A61F 7/02*      (2006.01)
*A61F 7/00*      (2006.01)

(52) U.S. Cl.
CPC ............. *A61H 9/0078* (2013.01); *A61F 7/02* (2013.01); *A61H 9/0092* (2013.01); *A61F 2007/0054* (2013.01); *A61H 2201/0207* (2013.01); *A61H 2201/0214* (2013.01); *A61H 2201/0242* (2013.01)

(58) Field of Classification Search
CPC ............. A61H 9/0092; A61H 9/0078; A61H 2201/0242; A61H 2201/0207; A61H 2201/0214; A61F 7/02; A61F 2007/0054
See application file for complete search history.

(56) References Cited

U.S. PATENT DOCUMENTS

| 4,149,541 | A | * | 4/1979 | Gammons ................. A61F 7/02 5/421 |
|---|---|---|---|---|
| 5,169,384 | A | | 12/1992 | Bosniak et al. |
| 5,437,610 | A | | 8/1995 | Cariapa et al. |
| 5,466,250 | A | | 11/1995 | Johnson, Jr. et al. |
| 5,584,798 | A | | 12/1996 | Fox |
| 5,662,695 | A | * | 9/1997 | Mason ................. A61F 5/05816 607/104 |
| 5,733,321 | A | | 3/1998 | Brink |
| 5,865,841 | A | | 2/1999 | Kolen et al. |
| 5,894,615 | A | | 4/1999 | Alexander |
| 5,925,010 | A | | 7/1999 | Caprio, Jr. |
| 5,989,285 | A | | 11/1999 | DeVilbiss et al. |
| 6,080,120 | A | | 6/2000 | Sandman et al. |
| 6,290,662 | B1 | | 9/2001 | Morris et al. |
| 6,352,550 | B1 | | 3/2002 | Gildersleeve et al. |
| 6,440,093 | B1 | | 8/2002 | McEwen et al. |
| 6,530,941 | B1 | | 3/2003 | Muller et al. |
| 6,551,347 | B1 | | 4/2003 | Elkins |
| 6,610,084 | B1 | | 8/2003 | Torres |
| 6,736,787 | B1 | | 5/2004 | McEwen et al. |
| 7,198,093 | B1 | | 4/2007 | Elkins |

(Continued)

*Primary Examiner* — Justine Yu
*Assistant Examiner* — Douglas Sul
(74) *Attorney, Agent, or Firm* — Olson & Cepuritis, Ltd.

(57) ABSTRACT

The subject matter of the invention relates to therapy wraps for the application of compression and/or thermal therapy to a patient. The wraps are formed of at least two layers of material which are sealed together to form at least one cavity between them. At least two layers of the wrap are sealed together using a plurality of different seal patterns. A first seal pattern is provided in at least one zone. The zone is surrounded by a perimeter seal, an internal seal or at least one different seal pattern or a combination thereof. The pattern within the zone or zones provides higher volume fluid flow paths than the pattern or patterns surrounding the zone or zones.

17 Claims, 6 Drawing Sheets

(56) References Cited

U.S. PATENT DOCUMENTS

| | | |
|---|---|---|
| 7,207,959 B1 | 4/2007 | Chandran |
| 7,211,104 B2 | 5/2007 | Edelman |
| 7,354,410 B2 | 4/2008 | Perry et al. |
| 7,396,345 B2 | 7/2008 | Knighton et al. |
| 7,442,175 B2 | 10/2008 | Meyer et al. |
| 7,896,910 B2 | 3/2011 | Schirrmacher et al. |
| D662,212 S | 6/2012 | Quisenberry |
| D662,213 S | 6/2012 | Quisenberry |
| D662,214 S | 6/2012 | Quisenberry |
| D664,260 S | 7/2012 | Quisenberry |
| D679,023 S | 3/2013 | Quisenberry |
| D683,042 S | 5/2013 | Quisenberry |
| 8,460,224 B2 | 6/2013 | Wilford et al. |
| 2005/0143797 A1 | 6/2005 | Parish et al. |
| 2005/0187501 A1 | 8/2005 | Ravikumar |
| 2007/0135743 A1 | 6/2007 | Meyer |
| 2008/0058911 A1 | 3/2008 | Parish et al. |
| 2009/0069731 A1 | 3/2009 | Parish et al. |
| 2010/0210982 A1 | 8/2010 | Balachandran et al. |
| 2012/0172774 A1* | 7/2012 | Lowe ............... A61F 7/02 602/13 |
| 2012/0172957 A1* | 7/2012 | Dewaegenaere ...... A61F 7/02 607/104 |
| 2012/0209153 A1 | 8/2012 | Farrow et al. |
| 2012/0209158 A1 | 8/2012 | Avitable et al. |
| 2014/0012169 A1 | 1/2014 | Wilford et al. |
| 2014/0222121 A1* | 8/2014 | Spence ........... A41D 13/005 607/104 |

\* cited by examiner

FIG. 5

THERAPEUTIC WRAP WITH PATTERN ZONE

CROSS-REFERENCE TO RELATED APPLICATION

Not Applicable

FEDERALLY SPONSORED RESEARCH OR DEVELOPMENT

Not Applicable.

BACKGROUND OF THE INVENTION

The present invention relates generally to thermal and compression systems used in the application of thermal and compression therapy to a patient's body. In practice, the wraps are connected to a thermal and compression machine that may supply compressed gas and a thermal fluid to the wrap. Generally, compressed gas may be pumped through a tube to the wrap while a thermal transfer fluid may be circulated through the wrap and machine by pumping fluid, that has been heated or cooled by the machine, from a reservoir in the machine through a tube connected to a wrap, circulating the fluid through the wrap, and allowing the fluid to exit the wrap through another tube which returns the fluid to the machine. An example of one such thermal and compression machine is described in U.S. Patent Application Publication 2011/0257565 filed on behalf of Wilford et al., the entirety of which is incorporated herein by reference.

More particularly, the invention is directed to removable wraps that are applied to a contoured portion or joint of the patient's body, for example, a patient's shoulder, ankle, leg or arm. The wraps include at least one fluid-tight chamber allowing for the ingress and egress of a fluid. The ingress of a fluid, which may also be heated or cooled, into the fluid-tight chamber applies compression and/or thermal therapy to the patient's body in the location of the wrap. Additionally, various layers of the wrap are sealed together at multiple locations, particularly within fluid chamber. The seals are arranged in patterns to form fluid pathways, and the size and location of the seals are varied so as to create multiple zones having differing seal patterns and thus differing fluid pathways. The locations of the differing zones ensure that the fluid pathways of the wrap remain open and prevent the wrap from kinking and terminating fluid movement through the wrap while optimizing the fluid and thermal transfer capacity of the wrap.

Compression and thermal wraps similar to the invention described herein have been in use for many years. For example, wraps constructed from multiple layers of fluid tight material and exhibiting fluid chambers having dot seal patterns are described in U.S. Patent Application Publication No. 2014/0012169 filed on behalf of Wilford et al., the entirety of which is incorporated herein by reference. The wraps are designed to be applied an area of the patient's body where therapy is desired. Once in place, a fluid (either a gas or a liquid) is forced into a fluid-tight chamber of the wrap thereby applying therapy to the portion of the patient's body contacted by the wrap. Such wraps are often used in the treatment and prevention of deep vein thrombosis and injury recovery but may have other uses as well.

One shortcoming of previous wraps is that they have a tendency to kink and shut off fluid flow when placed on a patient's joint, or other odd shaped body part. Kinking may also occur due to the weight of the patient's own body resting on the fluid wrap, for example, in the case of an ankle wrap the weight of a raised leg may place pressure on an ankle and thereby block fluid flow through the wrap. In the past, the solution was to provide large fluid pathways through the creation of large dot seals in the fluid chamber. However, the larger seal pattern allowed for a large volume of fluid to enter the wrap. The large fluid volume heavily taxed the thermal capacity of the thermal and compression machines providing fluid to the wrap and also added considerable weight to the wrap.

As described in detail below, the present invention provides a unique solution to the aforementioned problems.

SUMMARY OF THE INVENTION

The present invention relates to therapy wraps having a plurality of differing seal pattern zones. The wraps may be constructed of two or more layers of material which are sealed together to from a fluid tight cavity bounded by a cavity seal. Additionally, at least one hose is provided such that one end of the hose is in fluid communication with the interior of the cavity while the other end of the hose is in fluid communication with the environment. The hose may be provided with various valves to assist in the control of fluid moving from the environment into and/or out of the interior of the cavity.

Four differently shaped wraps are described herein to illustrate the various embodiments of the invention, though other wrap shapes could be utilized. For example, the one wrap is preferably in the shape of capital letter "I" having two elongated, horizontal members, generally in the shape of ovals, connected by a middle channel. The hose or hoses are positioned along one of the horizontal members such that fluid flowing through a hose is forced into a first member and then permitted to travel through the channel and into the second member. Preferably, the wrap is utilized to provide therapy to a person's knee or elbow. The channel is placed at the joint and the two horizontal members wrap around the limb above and below the joint. Due to the flex in the joint, the wrap has a tendency to bend in the area in and around the channel additionally, depending on the size of the patient and the positioning of the wrap and accompanying therapy machine, the area around the portion of the wrap where the fluid enters and exits the wrap (i.e. at the location of the hose or hoses) also tends to bend. That bending causes the layers of the wrap defining the fluid chamber to come together, kinking or creasing the wrap and blocking fluid flow.

To prevent that kinking, one or more zones of a first, large internal seal pattern are created around the locations in the fluid chamber where kinking occurs, such as around the fluid tubes and around the channel. The zones in those areas are provided with a pattern that is has comparatively large distances between each seal with respect to the seal pattern or patterns surrounding the perimeters of the zones. The area surrounding the perimeter of the zones, and preferable the area constituting the balance of the wrap is provided with a small seal pattern, where the distance between the seals forming the pattern are less than distances between the seals contained in the large seal pattern zones. The smaller pattern decreases the overall internal volume of the wrap, thereby limiting the total amount of fluid that can enter the wrap at a given time, while the large pattern zones ensure continuous fluid flow by providing larger pathways in critical areas and preventing kinking in those areas. Limiting the amount of fluid decreases the weight of the wrap when filled and reduces the thermal load on the thermal therapy device heating or cooling the wrap. That allows the thermal therapy device to more rapidly heat or cool the liquid, and hence wrap, thereby performing more efficiently and ensuring more reliable therapy.

The wraps constructed according to the present invention may be used to apply compression and thermal therapy to a body. It is contemplated that the wraps could be used to apply such therapy by using the wraps in conjunction with a compression and thermal therapy machine such as the device disclosed in U.S. Patent Application Publication No. U.S. 2001/0257565. That device is equipped with a number of ports which may be connected to the hose or hoses of the wraps discussed herein. The device provides fluid in the form of a thermal liquid or gas through the hoses connected to the ports and into the wraps in order to provide thermal and or compression therapy. Specific embodiments of various types of wraps and the locations of preferred pattern zones are set forth in more detail below.

DETAILED DESCRIPTION OF THE PREFERRED EMBODIMENTS

Throughout the specification, wherever practicable, like structures will be identified by like reference numbers.

It is preferable that the therapy system of the present invention is used to apply thermal and/or compression therapy utilizing various specially designed wraps. The particular shape and benefits afforded by the various specially designed wraps for use with the therapy system will be described in detail below. The wraps may be constructed for the application of thermal treatment using a circulated heated or cooled fluid, the application of compression therapy, or both. Thermal therapy only wraps may be constructed utilizing at least two layers of material and at least two hoses. The two or more layers of material and two or more hoses are laminated together at least about the perimeter of the two layers of material thereby forming a cavity between at least two or more layers and such that the two hoses provide pathways for the ingress and egress of fluid to and from the cavity. Alternately, the wrap designs could be utilized for compression therapy utilizing two or more layers of material and at least one hose. In such an embodiment the two or more layers of material and the at least one hose are sealed together about the perimeters of the material thereby forming a cavity between them with the one or more hoses providing a pathway for the ingress and egress of fluid, preferably compressed gas, to the cavity. In the preferred embodiments, the basic construction of each is essentially the same. Each wrap includes at least three, but preferably four, fluid tight layers of material and at least three hoses. The three or more layers of material and at least three hoses are sealed together, for example using radio frequency (RF) welding, so as to create at least two fluid tight chambers between them, such that fluid is permitted ingress to and egress from the chambers by way of the hoses. Material suitable for constructing wraps include 200 Denier nylon oxford laminated to urethane for use in creating the exterior layers, with interior layers being made of urethane alone. Such material may be purchased from a variety of companies including Lamcotec of 152 Bethany Road, PO Box 279, Monson, Mass. 01057.

It should be understood that the hose and/or hoses referred to herein are in the simplest sense pieces of conduit that provide an access pathway from the exterior of a fluid tight cavity to the interior of the fluid tight cavity. The hose may be of more complex design however, such as a multiple pieces of conduit having one or more valves or connection pieces all coupled together which essentially provide the same pathway between the exterior and interior of the fluid tight cavity. Preferably, the hose is simply a hose which provides the pathway between the interior of the cavity and the exterior of the fluid tight cavity by traversing the seal between the layers of material which define the fluid tight cavity. However, the hose could alternatively be a port which is formed in the sidewall of the fluid tight cavity to which another hose may be connected.

In the preferred construction of each of the wraps recited below, a first sheet of urethane is provided having at least one side coated with nylon. Preferably the nylon is coated on the outside of the layer intended to have contact with the skin so as to provide a barrier between the skin and urethane and to provide structural integrity for the wrap. The nylon side is placed face down such that the urethane side is facing up. Two hoses are place on top of the first sheet such that the hoses each cross over the perimeter of the first sheet and thus a first end of a first hose and a first end of a second hose each rest on top of the first sheet. The second end of the first hose and the second end of the second hose are each oriented such that each is in contact with the open air. Preferably, the hoses are oriented such that the longitudinal axis of each hose aligns perpendicularly to the perimeter of the first sheet at the point at which each hose crosses the perimeter of the first sheet. A second sheet of urethane material of substantially the same size and shape as the first sheet is oriented over the first sheet and laid on top of the first sheet such that the perimeters of both the first and second sheets substantially line up. The second sheet thus substantially covers the first sheet and covers the first end of the first hose and the first end of the second hose. A third sheet of urethane substantially the same size and shape as the first and second sheets is laid on top of the second sheet. A third hose is laid on top of the third sheet such that it crosses over the perimeter of the third sheet and thus a first end of the third hose rests on top of the third sheet. The second end of the third hose is oriented such that it is in contact with the open air. As with the first and second hoses, it is preferred that the third hose is oriented such that the longitudinal axis of the third hose aligns perpendicularly to the perimeter of the third sheet at the point at which the third hose crosses the perimeter of the third sheet. A fourth sheet of urethane coated with nylon, having substantially the same size and shape as the first, second and third sheets, is laid on top of the third sheet such that the perimeters of all four sheets substantially align; the fourth sheet covers the first end of the third hose and is laid on top of the other sheets such that the nylon coating is facing away from the third sheet.

The four sheets may then be sealed together, preferably about their perimeters. The seal is formed such that the first and second sheets are sealed together thereby creating a first cavity between the first and second sheet where the first and second hoses are sealed between the first and second sheets such that first end of the first hose and the first end of the second hose communicate with the cavity between the first and second sheets. Because the first end of the first hose and the first end of the second hose communicate with the first cavity and the second end of the first hose and the second end of the second hose communicate with the open air, fluid may be passed through the first or second hose to either fill or drain the first cavity. Similarly, the third sheet and fourth sheet are sealed together, preferably about their perimeters, thereby creating a second cavity between the third sheet and fourth sheet where the third hose is sealed between the third sheet and fourth sheet such that the first end of the third hose is in communication with the second cavity between the third sheet and fourth sheet. Because the first end of the third hose is in communication with the second cavity and the second end of the third hose is in communication with the open air, fluid may be passed through the third hose to either fill or drain the second cavity. The first, second, third and fourth sheets are also all sealed together, preferably about their perimeter, thereby creating one wrap having at least two cavities and two or more hoses such that a first cavity includes at least one hose in communication with the interior of the first cavity and a second cavity includes at least one hose in communication with the second cavity. It should be appreciated that the seals sealing together the first and second sheets and sealing together the third and fourth sheets form continuous paths encircling the entirety of the cavities formed between the first and second sheet and between the third and fourth sheet, respectively. The seal forming the first cavity further surrounds the exterior of the first and second hoses, while the seal forming the second cavity surrounds the exterior of the third hose such that the only avenue for fluid to ingress to and egress from the first cavity is through the first or second hoses and the only avenue for fluid to ingress to and egress from the second cavity is through the third hose. The wraps may also include fasteners, such as hook and loop, snaps, buttons, eyelets or other type of fasteners.

It should be apparent that additional hoses could be sealed between either the first and second layers or between the third and fourth layers or even between any number of additional layers. It should also be apparent that while it is preferable that the at least four layers of material are sealed together such that only one seal is necessary to form the first cavity, second cavity and connect the layers of material together, multiple seals could be utilized. That is, a first cavity seal could be used to seal together a first layer and a second layer to form a first cavity, a second cavity seal could be used to seal together a third layer and a fourth layer to form a second cavity and a third connecting seal could be used to seal at least one of the first or second layers of material to at least one of the third or fourth layers of material. The first cavity seal, second cavity seal, and connecting seal could each be of unique size and shape such that when the four layers of material are connected together along the connecting seal, none of the three seals overlap. Alternately, the three seals could partially overlap when the layers of material are connected together. Alternately, and preferably, all three seals, the first cavity seal, second cavity seal and connecting seal are all formed at the same time such that they are essentially one in the same seal, entirely overlapping and congruous with one another.

With respect to the wrap designs detailed herein, the wraps may be made of a single cavity, or, if multiple cavities are utilized, it is preferable that only one of the multiple cavities is provided with the various seal patterns described.

Bearing in mind the aforementioned general construction of the wraps, a number of specially designed wraps will now be described with reference to FIGS. 1 through 4.

Figure 1:
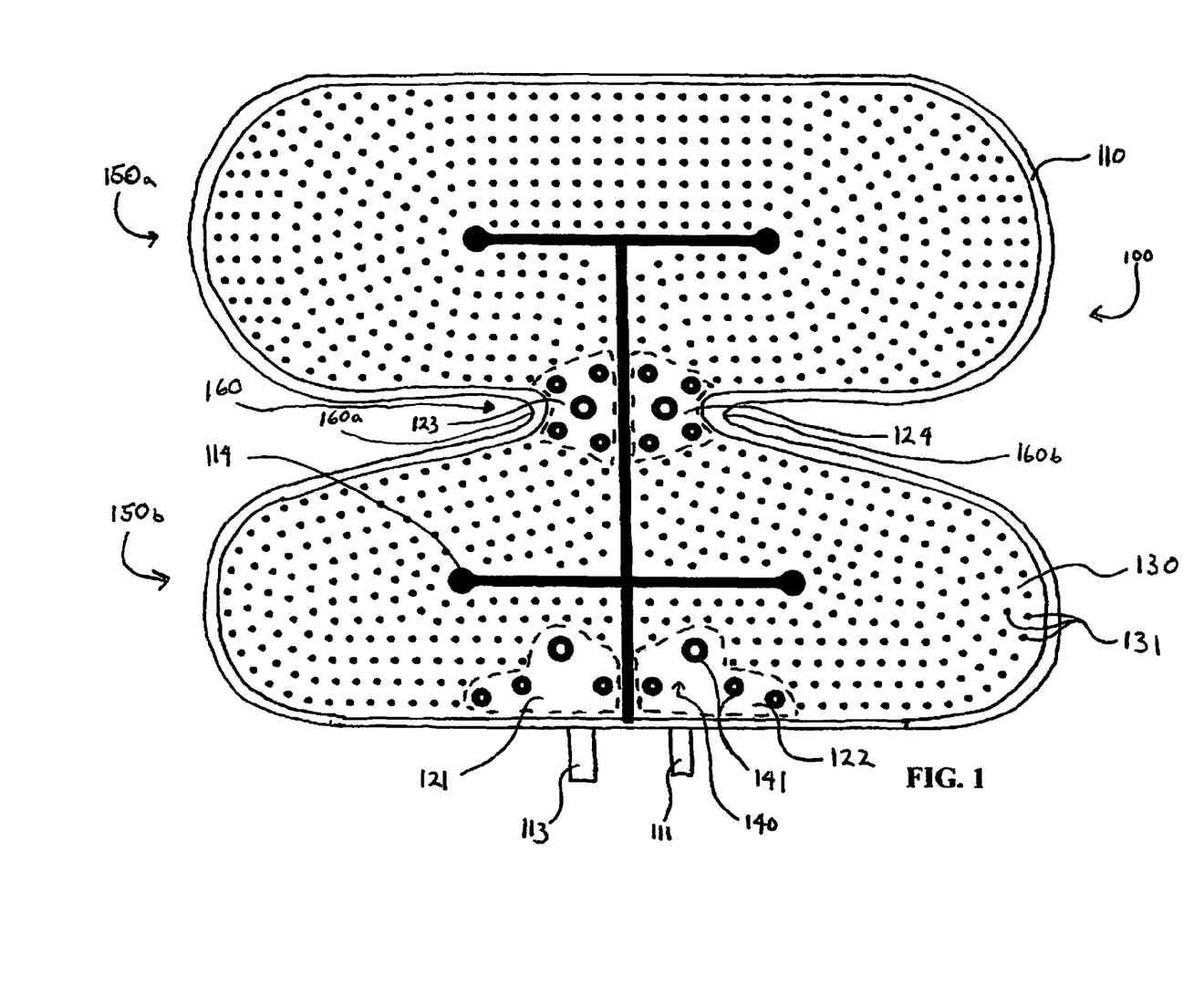
FIG. 1 is a plan view of a wrap having a shape similar to a capital letter "I" with fluid pathways and multiple seal patterns and zones that prevent fluid blockage and kinking. It may be referred to as a "joint wrap."

Referring now to FIG. 1, a wrap generally having the shape of a capital letter "I" is identified as 100. The wrap in FIG. 1 is constructed using two layers of material, all sealed together about perimeter or cavity seal 110 to form a cavity there between. It should be understood that additional layers and cavities could be added. In forming the wrap, a first layer of material is supplied, hoses, 111 and 113 are supplied and a second layer of material is supplied on top of the first layer. The first and second layers of material are sealed together about their perimeter so as to form a cavity between them where fluid may ingress to and egress from the cavity only by way of hoses 111 and 113.

The overall shape of the cavity of the warp depicted in FIG. 1 can generally be described as a two portions or lobes 150a and 150b joined by a narrow channel 160. As can be seen a cross-sectional line drawn through the fluid cavity along the narrowest portion of the channel (between points 160a and 160b) is shorter than any cross-sectional line, drawn parallel to the cross-sectional line of the channel and drawn through any portion of the fluid cavity contained within either portions 150a or 150b. It should be appreciated that the other wrap designs described in FIGS. 2 and 3 exhibit the same general construction.

An internal pathway seal 114 is also made, sealing layers one and two together and creating a fluid pathway from hose 111 around seal 114 to hose 113. While seal 114 may be of a variety of shapes, it is preferred that it simply mimics the shape of wrap 100, essentially bisecting the wrap into right and left parts while also extending into each of the ovals that form the top and bottom of the wrap. Thus, seal 114 has a proximal end that is connected to the cavity seal 110 between hose 111 and hose 113 and it has distal ends that terminate within the cavity. Seal 114 is said to be a pathway seal because it separates the fluid ingress and fluid egress tubs forcing fluid entering the wrap from the ingress tube to travel through a particular portion of the cavity and around the pathway seal 114 before reaching the egress tube and exiting the wrap. Wrap 100 is also provided with a plurality of additional pattern seals. Individual seals make up the overall pattern. Each seal has a seal area which is the area defined by the perimeter of the seal within which fluid is prevented from flowing. It should be appreciated that seals that are designed to be the same size might vary slightly in actual dimensions due to variances in the manufacturing process, but will be of substantially the same size and appear to be of the same size. The pattern seals are arranged to maximize fluid flow in particular areas of the wrap, prevent the wrap from kinking and shutting off fluid flow while simultaneously limiting the internal volume of the wrap and preventing the wrap from ballooning.

Figure 1A:
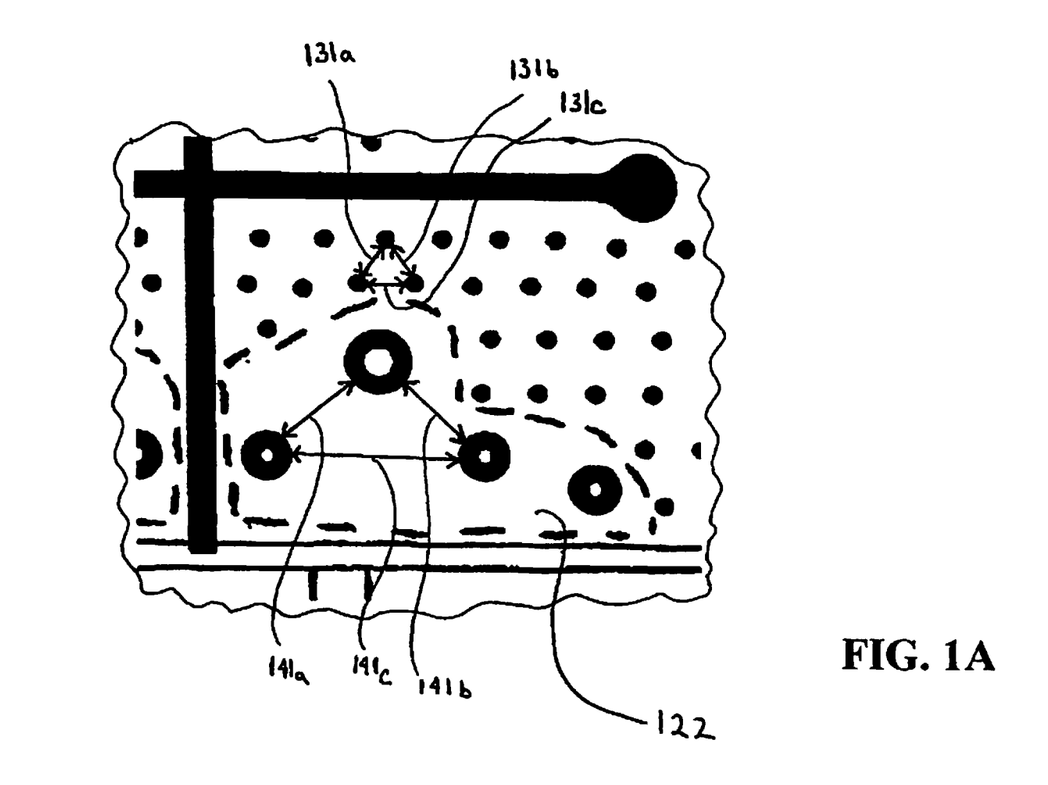
FIG. 1A is a blow up of the junction between a large pattern zone an alternate seal pattern in a wrap.

To accomplish the foregoing, a first pattern having relatively large dimensions is provided in at least one zone. A zone is an area of the wrap that has a perimeter defined by either a seal, such as seal 114 or perimeter seal 110, or another pattern or patterns that differ from the pattern in the zone, or a combination of one or more differing patterns and one or more seals. For example, the wrap in FIG. 1 has four zones, 121, 122, 123 and 124, each surrounded by a dashed line for explanative purposes. Looking at zone 122, it contains a pattern 140 and it is bordered on the bottom by perimeter seal 110, on the right and top by internal seal 114 and bordered on the left by pattern 130. As shown in FIG. 1, pattern 130 is different from pattern 140. Preferably, pattern 130 has smaller dimensions than pattern 140. As is shown, pattern 140 includes a number of circular seals, generally referred to by numeral 141, while pattern 130 includes a number of simple dot seals, generally referred to as 131. Additionally, in the preferred embodiment, the distances, shown as 131a, 131b and 131c in FIG. 1A, between any two adjacent dot seals 131, are each less than related distances, 141a, 141b and 141c, between adjacent pattern seals 141. Positioning the seals in that manner ensures that the pathways created between the seals 141 accommodate a greater volume of fluid that the pathways between seals 131 such that the zone 121 provides for greater fluid flow than a similar sized area having the alternate pattern 130. It is preferred that the surface area of the cavity defining the zones constitutes a minority of the surface area of the cavity while the surface area of the cavity containing the one or more patterns differing from the pattern or patterns contained within the zones constitutes the majority of the surface area of the cavity.

Figure 5:
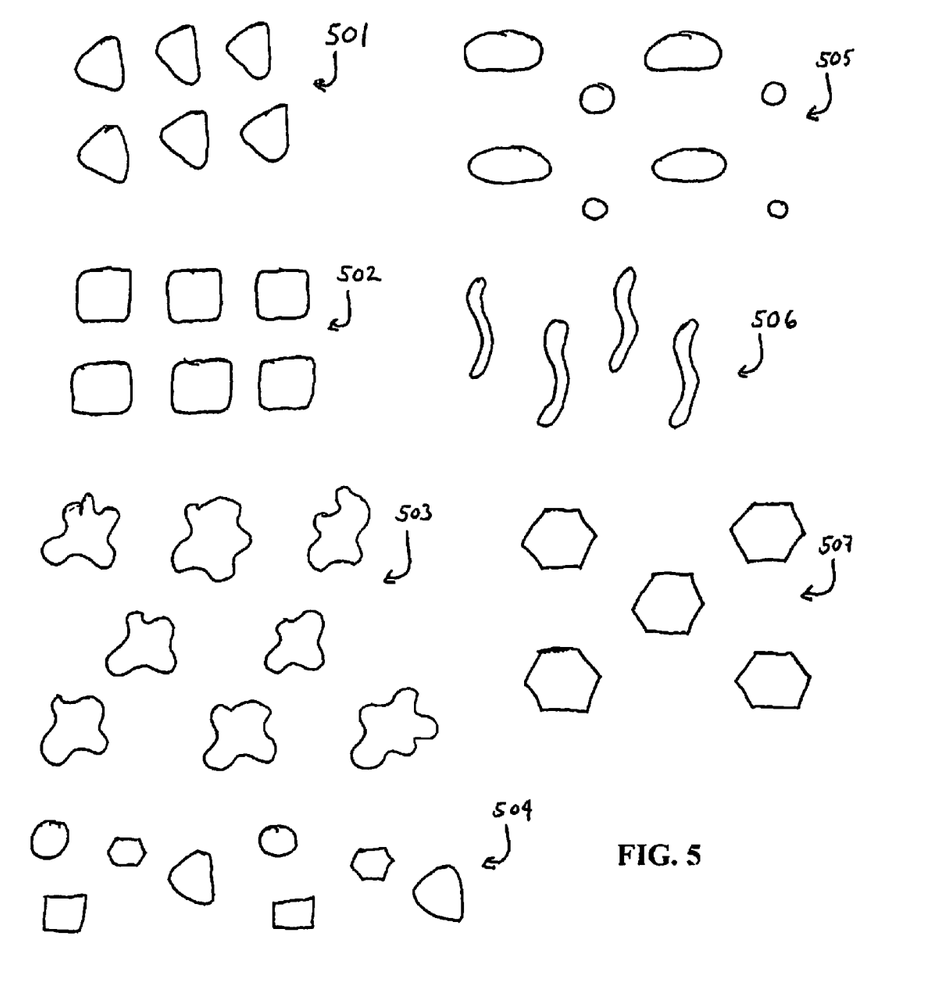
FIG. 5 is a generic example of differing sealing pattern zones.

It should be recognized that while the particular shapes of the seals 131 and 141 are shown as dots and circles, respectively, they are not limited to those shapes. Circular seals are shown for explanative purposes only and represent only a simple shape, easily formed in the material forming the layers of the wrap. Circular patterns also ensure uniform displacement of wrap layer material during the sealing process and help ensure that pressure points are not formed in the seals. Pressure points tend to occur at sharp edges. When the wrap fills with fluid, the wrap layers tend to pull apart at the sharp edge pressure point and tear the layers of material. Consequently, while any shape of pattern seal could be used, it is preferred that the pattern seal be provided with a smoothly curved perimeter, such as a circle or oval. Examples of other shapes and differently patterned zones are shown in FIG. 5. Additionally, while the multiple zones 121, 122, 123 and 124 are each shown as having the same seal pattern, it should be appreciated that the seal patterns in those zones need not be the same.

In the preferred embodiment of the wrap shown in FIG. 1, the zones 121, 122, 123 and 124 are located at particular problem areas. Zones 121 and 122 are provided at the inlet and outlet hoses 111 and 113. Placement around the hoses ensures that fluid flow is will not be interrupted as fluid enters and exits the wrap. Zones 123 and 124 are placed in the approximate location where a patient's joint would be and where previously manufactured wraps kinked, shutting off fluid flow. In practice, the wrap is placed on a patient joint, such as a knee, where the flaps of the top and bottom ovals are allowed to wrap around the leg on the top and bottom of the knee joint. When a patient's leg bends it will bend the wrap at the location of zones 123 and 124, but the larger pattern zones will maintain fluid flow through those areas and prevent the wrap from kinking.

Figure 2:
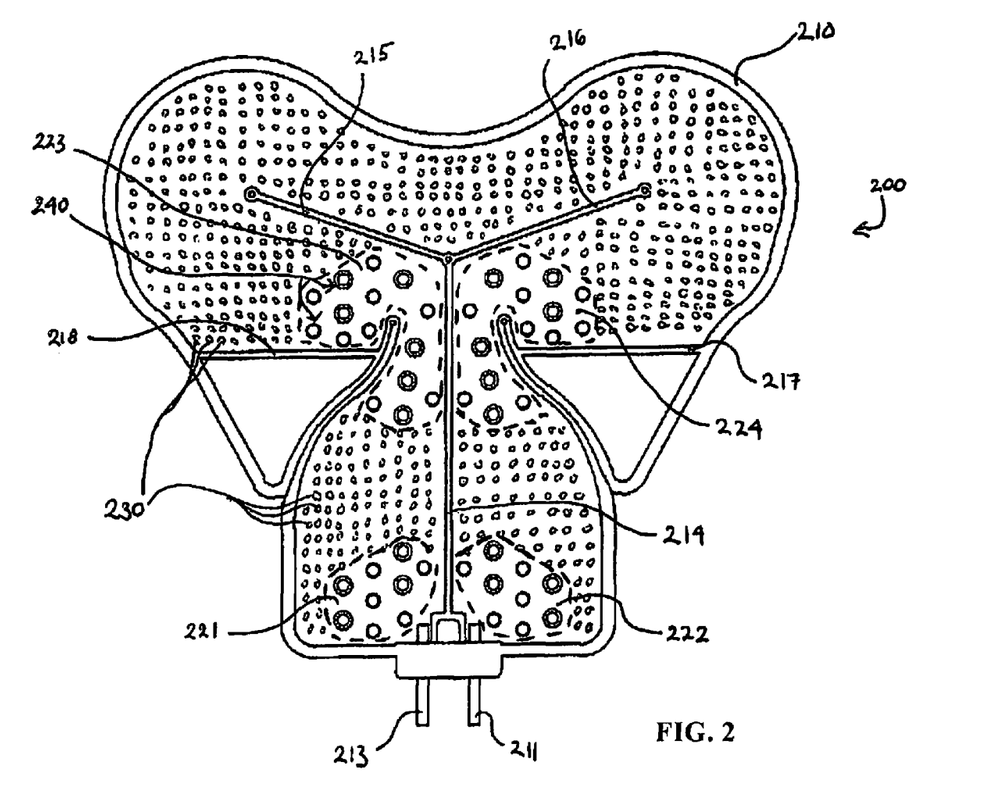
FIG. 2 is a plan view of a wrap having a shape similar to the capital letter T or Y with fluid pathways and multiple seal patterns and zones that prevent fluid blockage and kinking. It may be referred to as a "shoulder wrap."

Referring to FIG. 2 another wrap 200 is provided. It should be appreciated that the method of construction of wrap 200 may be achieved in essentially the same manner as the construction of wrap 100, particularly with respect to sealing multiple sheets and hoses together to form one or more cavities between the sheets so as to only allow for the ingress and egress of fluid through the hoses. The shape of wrap 200 is different however, essentially being triangular or clover like, or in a broad sense as the shape of the capital letter Y or T.

Depicted in FIG. 2 is one side of wrap 200. It has perimeter seal 210, hoses 211 and 213 and internal pathway seals 214, 215 and 216. The internal seals form a fluid pathway in the cavity such that fluid entering the cavity from hose 211 is forced around the seals in the cavity before it may egresses from hose 213. Other internal seals 217 and 218 may also be formed in order to direct fluid flow. As with the other wraps described herein, pattern seals are also be formed in wrap 200.

The wrap in FIG. 2 has four zones, 221, 222, 223 and 224, each surrounded by a dashed line for explanative purposes. Looking at zone 223, it contains a pattern 240 and it is bordered on all sides by either different pattern 230, an internal seal (215, 214, 218) or perimeter seal 210. Again, pattern 230 is different from pattern 240 in the same way that pattern 130 differs from pattern 140 in FIGS. 1 and 1A.

The zones 221 and 222 are placed at the location of the tubes. Zones 223 and 224 are placed in the area of the wrap that flexes when applied to a patient. Wrap 200 is designed to be placed on a patient's shoulder, with the ball of the shoulder being placed in the middle of the "Y", the portion of the wrap containing the tubes hanging down and the balance of the wrap being curved around the patients shoulder, chest and back areas. The curving of the wrap tends to king the flex point just below the middle of the "Y". Consequently, the zones having the large seal pattern are placed at that location to ensure proper fluid flow and prevent the wrap from kinking.

Figure 3:
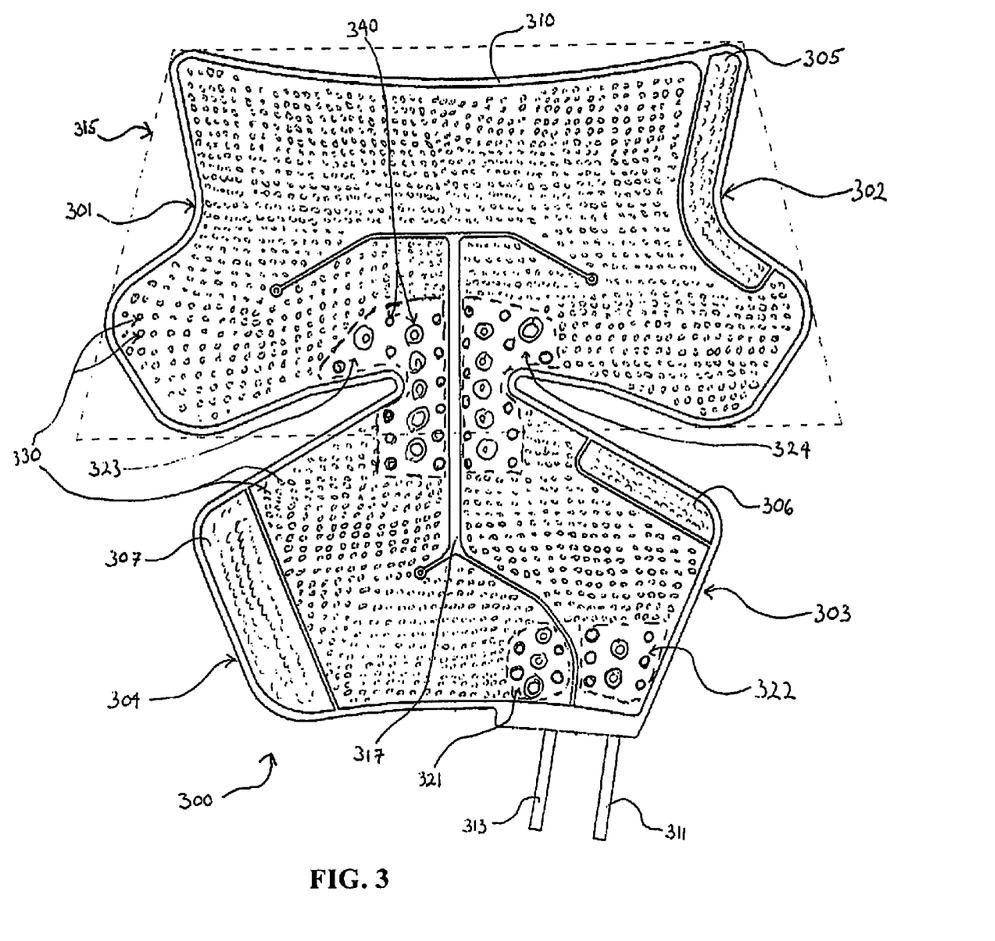
FIG. 3 is a plain view of a wrap having a shape similar to that of a trapezoid connected to a pentagon with fluid pathways and multiple seal patterns and zones that prevent fluid blockage and kinking. It may be referred to as an "ankle wrap."

FIG. 3 depicts another wrap, 300, designed to accommodate a patient's foot, ankle and lower calf. The basic construction of wrap 300 is similar to the other wraps discussed herein. In the embodiment depicted, only a single cavity wrap is shown where two hoses, 311 and 313 are provided to allow for fluid to ingress to and egress from the cavity. Wrap 300 includes four lobes, 301, 302, 303, and 304. The overall shape of the wrap, defined by perimeter seal 310, is essentially symmetrical when bisected along a longitudinal axis. That is, lobe 301 mirrors lobe 302 and lobe 303 mirrors lobe 304. Within the wrap a fluid pathway seal 314 is formed.

The basic shape of wrap 300 is that of a trapezoid joined to a pentagon. The trapezoid may be said to have a top and a base, where the length of the top is less than the length of the base, and the sides form acute angles as they extend away from the base toward the top while also forming obtuse angles as they extend away from the top toward the base. The pentagon may be said to be formed of a triangle and a trapezoid, where one side of the triangle forms the base of the trapezoid, and the point of the triangle, opposite that base, constitutes the top of the pentagon.

The two upper lobes, 301 and 302, generally form a trapezoid (roughly outlined by hash line 315), each lobe 301 and 302 forming half of the trapezoidal shape, while the two lower lobes, 303 and 304, generally form a pentagon, each lobe 303 and 304 forming half of the pentagonal shape. All of the lobes meet approximately in the middle of the base trapezoid formed by lobes 301 and 302, and at the top point of the pentagon formed by lobes 303 and 304 thereby forming a cavity bounded by seal 310.

The shape of wrap 300 is designed to allow the wrap to conform to the unique shape of an individual's foot, ankle and lower calf. In practice, an individual aligns his foot such that the individual's heal is placed in the upper trapezoidal portion, the individual's arch bridges the connection point between the upper and lower portions, and the individual's toes are located in the pentagonal section, oriented closest to hoses 311, 312, and 313. To secure the wrap 300, lobe 301 is lifted up then wrapped around the individual's ankle. Lobe 302 is lifted up and wrapped over lobe 301, also around the individual's ankle. Fastener segment 305, which includes a fastener such as hooks, is then secured to the exterior of lobe 301. Thus the upper portions of lobes 301 and 302 surround the individual's ankle and lower calf. Lobes 604 and 603 are folded over the foot and secured using fasteners 606 and 607.

When securing the wrap as described the meeting point between the trapezoid top and the pentagon bottom flexes. To ensure proper fluid flow, zones 323 and 324 having seal patterns are formed at that middle location. As described in connection with other wraps discussed herein, the patterns within the zones are larger that the patterns in the areas surrounding the zones. Similarly, zones 321 and 322 are formed at the area where the tubes 311 and 313 enter the wrap. Thus, similar to the wrap described in FIG. 1, wrap 300 has four zones, 321, 322, 323 and 324, each surrounded by a dashed line for explanative purposes. Zone 323, for example, contains a pattern 340 and it is bordered on all sides by either different pattern 330, internal fluid pathway seal 314 or perimeter seal 310. Again, pattern 330 is different from pattern 340 in the same way that pattern 130 differs from pattern 140 in FIGS. 1 and 1A.

Figure 4:
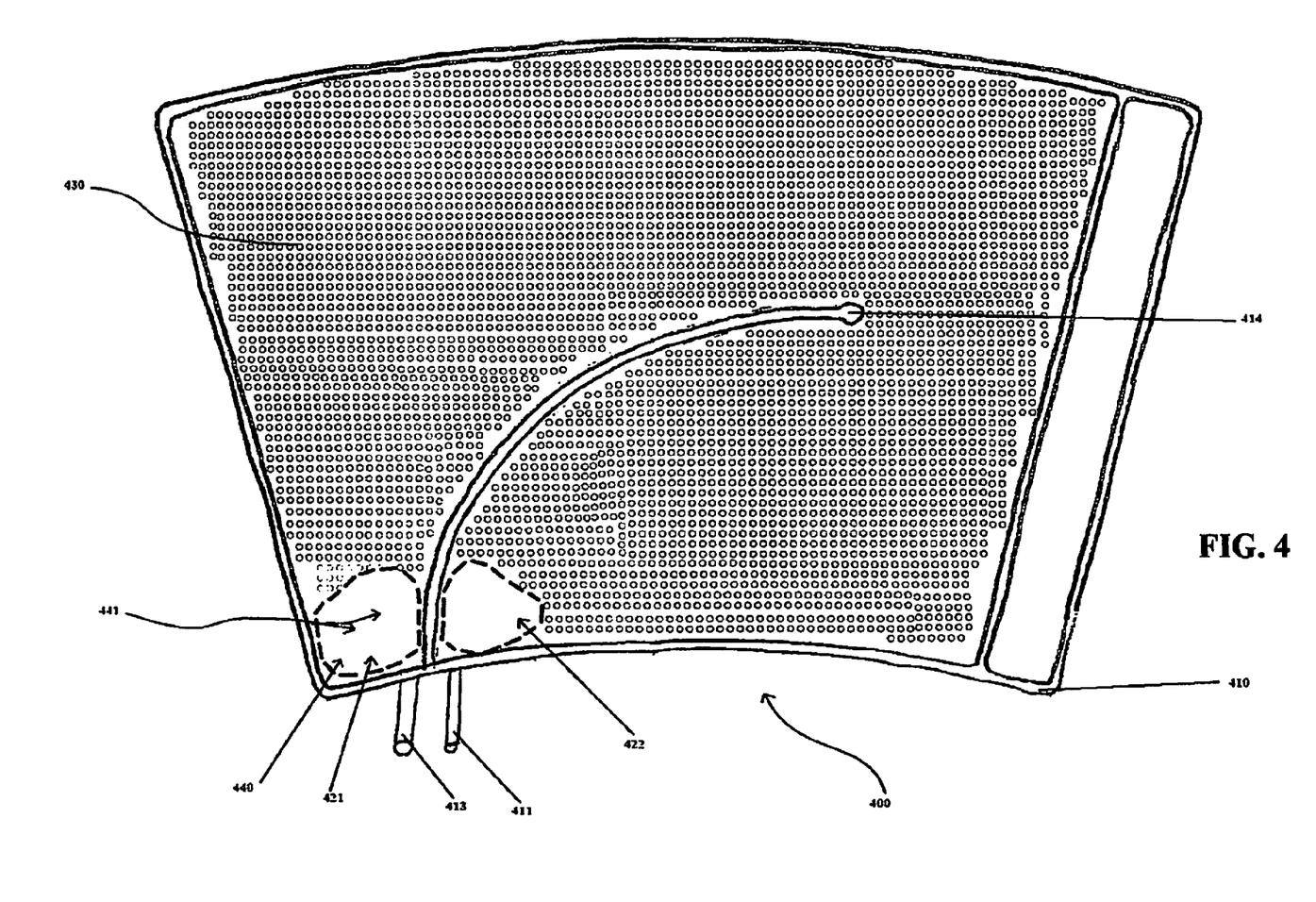
FIG. 4 is a plan view of a wrap having a shape similar to a trapezoid with fluid pathways and multiple seal patterns and zones that prevent fluid blockage and kinking. It may be referred to as a "knee wrap."

Another embodiment is shown in FIG. 4. Wrap 400 is generally trapezoidal in shape, has a perimeter seal 410, and an internal pathway seal 414. It is constructed similarly to the wraps described above, and contains a fluid cavity with hoses 411 and 413 providing a path for the ingress and egress of a fluid. Wrap 400 is generally used to surround a patients arm or leg. Consequently, the areas of most concern respecting fluid flow are found at the entry of the tubes. Just as described with respect to the other wraps detailed above, patterned zones 421 and 422 are formed at the location of the tubes. Thus, similar to the wrap described in FIG. 1, wrap 400 has two zones, 421 and 422, each surrounded by a dashed line for explanative purposes. Zone 421, for example, contains a pattern 440 and it is bordered on all sides by either different pattern 430, internal fluid path seal 414 or perimeter seal 410. Again, pattern 430 is different from pattern 440 in the same way that pattern 130 differs from pattern 140 in FIGS. 1 and 1A.

As shown in FIG. 5, any number of differing patters could be used to form the seal patterns within the zones. By way of non-limiting example, patterns include triangular shapes 501, square shapes 502, non-uniform shapes 503, a mix of different shapes 504, ovals and circles 505, lines 506, hexagons 507 and others. The patterns within the zones provide fluid paths that accommodate a greater volume of fluid that the fluid pathways formed in the surrounding area. It is preferable that the zones are provided with the pattern having larger volume fluid pathways while all other areas of the wrap are provided with one or more different patters such that the patters not contained within the zones have lower volume fluid pathways than the pathways formed by the patterns within the zones. The lower volume pathways limit the overall volume of the wrap, as compared to a wrap formed with only the larger pattern contained in the zone. Limiting the volume of fluid ensures that the thermal therapy machine is able to maintain the proper temperature of fluid and it also decreases the overall weight of the wrap when fully filled. It should also be appreciated that while the preferred embodiments discussed herein utilize an alternate pattern comprising simple dot seals, seals having different sizes or shapes could be utilized to form the seals outside of the different zones.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A therapy wrap comprising:
    two or more layers of material and one or more hoses
        wherein a first layer of material and a second layer of material are sealed together along a first cavity seal such that a first cavity is formed between the first and second layer;
    wherein said hose is provided such that a first end of said hose is exterior to the first cavity and a second end of said hose is interior to the first cavity;
    wherein said first cavity contains a plurality of first pattern seals forming a first pattern, said first pattern seals have a small circumference and seal together portions of said first layer of material and said second layer of material at a plurality of locations within said first cavity;
    wherein said first cavity further contains a plurality of second pattern seals forming a second pattern, said second pattern being different than said first pattern, said second pattern seals seal together portions of said first layer of material and said second layer of material at a plurality of locations within said first cavity;
    wherein said second pattern seals include medium seals and large seals each having a circumference such that said large seals have a circumference greater than the circumference of the medium seals and the medium seals have a circumference greater than the small circumference of the first pattern seals such that the seals forming the second pattern have circumferences greater than the circumference of the first pattern seals;
    wherein said second pattern seals are formed within at least one zone and
    wherein said medium seals are formed in at least one straight line and said large seals are formed in at least one straight line such that centers of the medium seals and centers of the large seals are offset.

2. The therapy wrap of claim 1 wherein said first cavity has a cavity surface area and a total surface area of said cavity containing said first pattern seals constitutes a majority of the cavity surface area.

3. The therapy wrap of claim 1 wherein said first cavity seal forms single curved line and a majority of said first pattern seals are formed in a curvilinear manner that approximates the curved line of the first cavity seal.

4. The therapy wrap of claim 1 wherein at least one zone is oriented so as to surround an area of said first cavity containing said second end of said hose such that fluid entering said first cavity through said hose must enter said zone before flowing into any other area of said first cavity.

5. The therapy wrap of claim 4 further comprising at least a first zone and a second zone, such that said first zone is oriented so as to surround an area of said second end of said hose and said second zone is separated from said first zone such that fluid traversing said first cavity must flow through said first zone and flow through an area of said first cavity containing said first pattern before entering said second zone.

6. The therapy wrap of claim 1 further comprising at least two hoses, each hose having a first end and a second end wherein said first ends of each hose are located outside of said first cavity and said second ends of said hoses are located within said cavity and wherein at least one zone is oriented so as to surround areas of said first cavity containing said second ends of said hoses such that fluid entering said first cavity through either of said second ends of said hoses must enter at least one zone before flowing into any other area of said first cavity.

7. The therapy wrap of claim 6 wherein a first zone surrounds one of said second ends of said hoses and wherein a second zone surrounds another second end of said hoses.

8. The therapy wrap of claim 7 wherein said first zone and said second zone are separated by at least one pathway seal such that fluid entering said cavity and flowing through said first zone must exit said first zone and flow through an area of said cavity containing said first pattern seals before entering said second zone;
 wherein the large seals in said first zone and the large seals in said second zone are formed a straight line between them; and
 wherein the medium seals in said first zone and the medium seals in said second zone are formed a straight line between them.

9. The therapy wrap of claim 1 wherein an area of the first cavity containing said first pattern is area one and has a first maximum fluid volume, and wherein an area of said first cavity containing said zone is area two and has a second maximum fluid volume such that when area one is equal to area two, said second maximum fluid volume is greater than said first maximum fluid volume.

10. The therapy wrap of claim 1 wherein said first pattern is defined by a plurality of repeating seals that form a first pattern and wherein adjacent seals of said first pattern are separated by a number of first distances;
 wherein said second pattern is defined by a plurality of repeating seals that form a second pattern and wherein adjacent seals of said second pattern are separated by a number of second distances; and
 wherein said first distances are less than related ones of said second distances.

11. A therapy wrap comprising:
 two or more layers of material and at least a first hose and a second hose wherein a first layer of material and a second layer of material are sealed together along a first cavity seal such that a first cavity is formed between the first and second layer;
 wherein said first hose and said second hose are each provided such that a first end of each hose is exterior to the first cavity and a second end of each hose is interior to the first cavity;
 wherein said first cavity contains at least one pathway seal;
 wherein said first cavity contains a plurality of first pattern seals forming a first pattern, said first pattern seals have a small circumference and seal together portions of said first layer of material and said second layer of material at a plurality of locations within said first cavity;
 wherein said first cavity further contains a plurality of second pattern seals forming a second pattern, said second pattern being different than said first pattern, said second pattern seals seal together portions of said first layer of material and said second layer of material at a plurality of locations within said first cavity, said second pattern seals being formed within a first zone;
 wherein said first cavity further contains a plurality of third pattern seals forming a third pattern, said third pattern being different than said first pattern, said third pattern seals seal together portions of said first layer of material and said second layer of material at a plurality of locations within said first cavity, said third pattern seals being formed within a second zone; and
 wherein said first cavity further contains a plurality of fourth pattern seals forming a fourth pattern, said fourth pattern being different than said first pattern, said fourth pattern seals seal together portions of said first layer of material and said second layer of material at a plurality of locations within said first cavity, said fourth pattern seals being formed within a third zone;
 wherein said second pattern seals, said third pattern seals, and said fourth pattern seals each include medium seals and large seals each having a circumference such that said large seals have a circumference greater than the circumference of the medium seals and the medium seals have a circumference greater than the small circumference of the first pattern seals such that the the second, third and fourth pattern seals have circumferences greater than the circumference of the first pattern seals; and
 wherein said medium seals are formed in at least one straight line and said large seals are formed in at least one straight line such that centers of the medium seals and centers of the large seals are offset.

12. A therapy wrap as in claim 11 wherein said first zone, said second zone and said third zone are oriented within said first cavity such that fluid entering said first cavity through said first hose and exiting said cavity through said second hose must flow through said first zone before flowing into said second zone and must flow through said second zone before flowing into said third zone and must flow through said third zone before flowing through said second hose.

13. A therapy wrap as in claim 11 wherein said first zone surrounds the second end of said first hose and wherein said third zone surrounds the second end of said second hose.

14. A therapy wrap as in claim 11 wherein said first zone, said second zone and said third zone are separated by areas containing said first pattern such that fluid flowing between said first and second zones must flow through an area of said first cavity containing said first pattern, and wherein fluid flowing between said second zone and said third zone must flow through an area of said first cavity containing said first pattern.

15. A therapy wrap as in claim 11 wherein an area of the first cavity containing said first pattern is area one and has a first maximum fluid volume, and wherein an area of said first cavity containing at least one of said first zone, said second zone or said third zone is area two and has a second maximum fluid volume such that when area one is equal to area two, said second maximum fluid volume is greater than said first maximum fluid volume.

16. A therapy wrap as in claim 11 further comprising a first area, said first area being an area defined within the first cavity containing said first pattern and having a first maximum fluid volume such that a second area that is equal to that of said first area, but which is defined within any zone, has a second maximum fluid volume; and
 wherein said second maximum fluid volume is greater than said first maximum fluid volume.

17. The therapy wrap of claim 11 wherein said first cavity seal forms single curved line and a majority of said first pattern seals are formed in a curvilinear manner that approximates the curved line of the first cavity seal.

* * * * *

UNITED STATES PATENT AND TRADEMARK OFFICE
CERTIFICATE OF CORRECTION

PATENT NO. : 9,510,994 B2
APPLICATION NO. : 14/175790
DATED : December 6, 2016
INVENTOR(S) : Michael L. Wilford and Fernando A. Ubidia Page 1 of 1

It is certified that error appears in the above-identified patent and that said Letters Patent is hereby corrected as shown below:

In the Specification

Column 1, Line 57, delete "applied an area" and insert --applied to an area--;
Column 4, Line 23, delete "such as a multiple" and insert --such as multiple--;
Column 4, Line 40, delete "are place on" and insert --are placed on--;
Column 7, Line 51, delete "is will not" and insert --will not--;
Column 8, Line 12, delete "are also be" and insert --may also be--;
Column 8, Line 29, delete "king" and insert --kink--;
Column 9, Line 18, delete "larger that" and insert --larger than--;
Column 9, Line 47, delete "patters" and insert --pattern--;
Column 9, Line 57, delete "patters" and insert --pattern--;
Column 9, Line 58, delete "patters" and insert --pattern--;

In the Claims

Claim 8, Column 11, Line 22, delete "formed a straight" and insert --formed in a straight--;
Claim 8, Column 11, Line 25, delete "formed a straight" and insert --formed in a straight--;
Claim 11, Column 12, Line 7, delete "zone; and" and insert --zone;--.

Signed and Sealed this
Ninth Day of May, 2017

Michelle K. Lee
*Director of the United States Patent and Trademark Office*